United States Patent
Cronin

[11] Patent Number: 5,810,743
[45] Date of Patent: Sep. 22, 1998

[54] TWO PIECE NEURODIAGNOSTIC TEST INSTRUMENT WITH DISPOSABLE TEST HEAD AND WEIGHTED REUSABLE HANDLE

[76] Inventor: Gary L. Cronin, P.O. Box 1347, Idaho Springs, Colo. 80452

[21] Appl. No.: 738,823

[22] Filed: Oct. 28, 1996

Related U.S. Application Data

[63] Continuation-in-part of Ser. No. 431,555, May 1, 1995, abandoned.

[51] Int. Cl.$^6$ ................................................. A61B 19/00
[52] U.S. Cl. ................................................................ 600/557
[58] Field of Search ..................... 128/740, 744, 128/774; 601/128, 129; 606/181

[56] References Cited

U.S. PATENT DOCUMENTS

| | | | |
|---|---|---|---|
| 3,515,125 | 6/1970 | Ruskin | 128/744 |
| 4,343,185 | 8/1982 | Knute | 374/158 |
| 5,433,212 | 7/1995 | Greenfield | 128/744 |
| 5,474,084 | 12/1995 | Cunniff | 128/744 |

*Primary Examiner*—Max Hindenburg
*Attorney, Agent, or Firm*—Edwin H. Crabtree; Ramon L. Pizarro; Donald W. Margolis

[57] ABSTRACT

A two piece neurodiagnostic test instrument sensitive to the prevalence of blood borne pathogens in a clinical environment. The test instrument provides a weighted balance to conduct a proper neurodiagnostic test without fear of puncturing a patient's skin. The instrument alone and without additional force applied by the physician provides the necessary weight to achieve accuracy and consistency during an examination procedure. The test instrument includes a weighted stainless steel reusable handle with a disposable plastic pinwheel test head releasably attached thereto. The test head includes a first end with coupling arms which are inserted into a receptacle in a first end of the weighted handle. A second end of the test head includes a rotatable pin wheel with a shroud disposed around an upper portion of the pin wheel. The weighted handle includes a hollow elliptical tube with a spring biased ejector bar received inside the tube. One end of the ejector bar, which is used as an ejector button, extends outwardly from a second end of the tube. Upon the completion of a clinical test, the ejector button is pushed and the ejector bar urges the test head outwardly from the first end of the handle. The test head is discharged and received inside a waste container for disposal thereby allowing a physician to never contact the test head after its use.

10 Claims, 2 Drawing Sheets

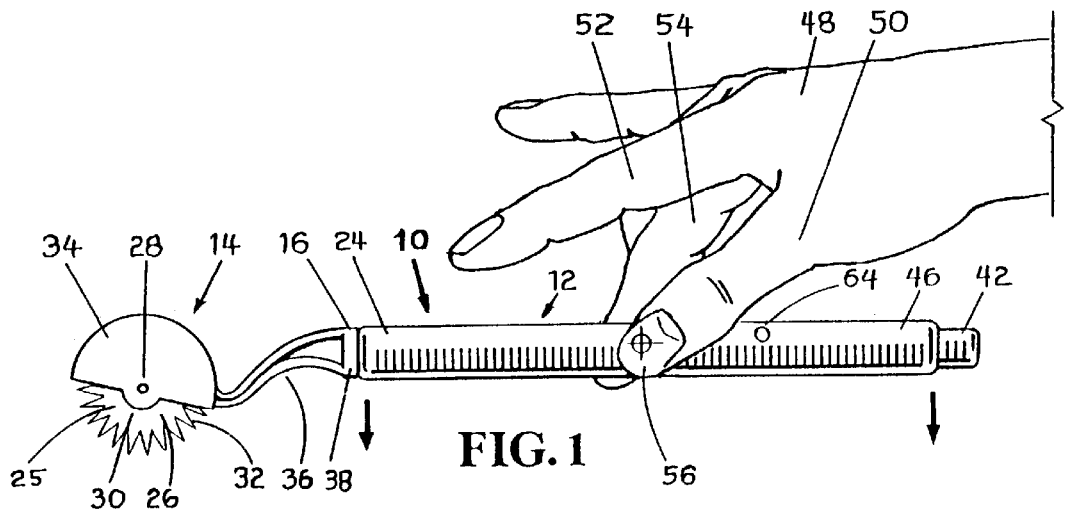
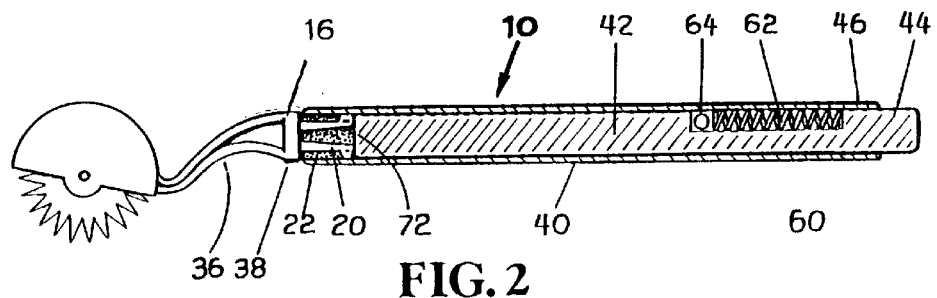
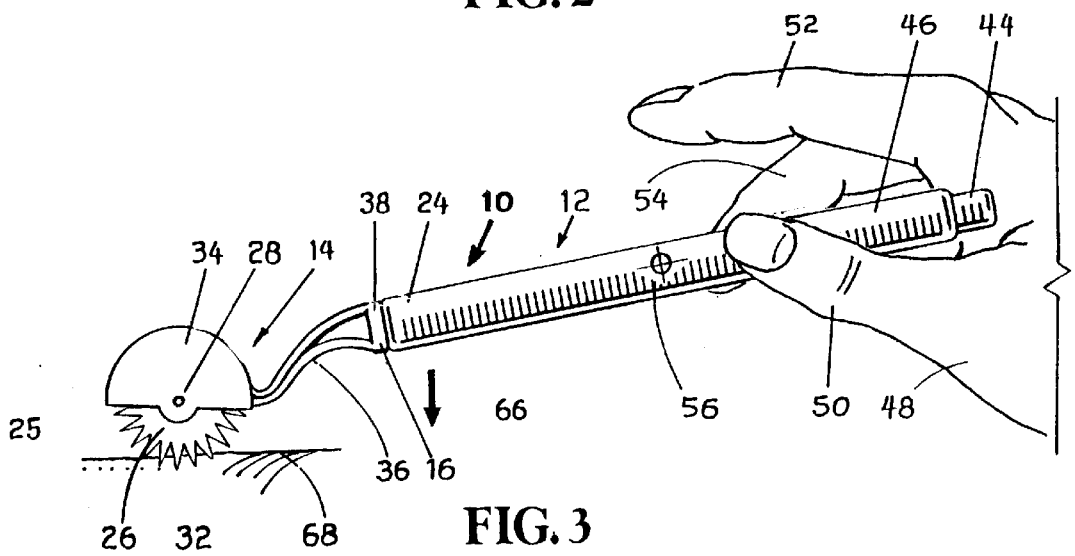

TWO PIECE NEURODIAGNOSTIC TEST INSTRUMENT WITH DISPOSABLE TEST HEAD AND WEIGHTED REUSABLE HANDLE

The subject utility patent application is a continuation-in-part of the applicant's patent application, Ser. No. 08/431,555, filed on May 1, 1995, now abandoned.

BACKGROUND OF THE INVENTION (a) Field of the Invention

This invention relates to neurological diagnostic test instruments in the medical field and more particularly, but not by way of limitation, to a neurodiagnostic test instrument for dermatomal sensory testing by a physician with patients in the testing of nerve sensation. Dermatome being an area of the skin supplied with afferent (sensory) nerve fibers by a single posterior spinal (nerve) root.

(b) Discussion of Prior Art

In the field of medicine, a need has been established to accurately and consistently test nerve sensation. In the past, the sensory nerve function has been crudely tested using objects such as needles, paper clips, toothpicks or other such devices. The subject invention is a predecessor to a weighted test instrument called the "Wartenberg Pinwheel". This instrument comprises a forked steel handle and a steel pinwheel secured to the fork. The weight of the Wartenberg Pinwheel provides for traditional testing of patients without the physician having to apply force to the pinwheel when it engages the surface of a patient's skin. Also, this early test instrument served the need for accuracy and consistency in gathering data concerning nerve sensation by virtue of its weight.

The quality of neurological testing is crucial in diagnostic procedures when there is a potential for nerve damage. In order to achieve accurate findings in gathering test results, it is essential that the test be performed with consistency. The Wartenberg Pinwheel, when properly used, allows for a consistent weight to bear on the skin (dermatome) of the patient and will therefore provide consistent and accurate findings. To use the Wartenberg Pinwheel properly, the handle of the instrument is held between the thumb and the middle finger of the doctor or tester. The test is performed by stroking the pinwheel on the skin of the patient and allowing only the weight of the instrument to provide a consistent weight on the skin during the test.

With the recent onslaught of blood borne pathogens specifically HIV and Hepatitis B and C, the Wartenberg Pinwheel has become suspect in cross contamination. If a patient was to move during the test procedure, it would be possible to penetrate the skin and contaminate the test instrument. If the patient possessed any open lesions in the test area (dermatome), the instrument could also become contaminated. Since this instrument is not normally sterilized between uses, it is possible to contaminate the next patient. Also, it is possible that the testing physician could be contaminated.

Heretofore there have been a variety of different types of lightweight test instruments with detachable pin wheel heads as described in U.S. Pat. No. 5,316,012 to Siegal and U.S. Pat. No. 5,474,084 to Cunniff. Also in U.S. Pat. No. 5,222,504 to Solomon a light weight plastic test instrument is described. In U.S. Pat. No. 3,515,125 to Ruskin, U.S. Pat. No. 3,344,781 to Allen and Russian Patent SU 1748792-AI describe the more traditional neurological diagnostic tools.

None of the above mentioned patents disclose, teach and provide the advantages of a combination of a weighted reusable handle with a disposable plastic pinwheel test head as described herein.

SUMMARY OF THE INVENTION

In view of the foregoing, it is a primary object of the present invention to provide the medical community with a two piece neurodiagnostic test instrument sensitive to the prevalence of blood borne pathogens in a clinical environment. The test instrument provides a weighted balance to conduct a proper neurodiagnostic test without fear of puncturing a patient's skin.

Another object of the invention is to provide the necessary weight in the test instrument which achieves repeated accuracy and consistency during ongoing examination procedures of a patient.

Still another object of subject instrument is unlike other lightweight plastic test instruments with a pin wheel and a handle, there is no need for a physician to apply additional force during a test procedure. The subject invention possesses the optimum weight for consistent pressure during the test procedure.

Yet another object of the instrument is the disposablilty of the pinwheel test head that becomes potentially contaminated when it comes into direct contact with the patient's skin. Since the disposable test head can be manually ejected from the weighted handle, the doctor or tester is in no danger of contamination through contact with the test head.

A further object of the invention is the pinwheel test head is partially covered with a protective shroud. The shroud serves to guard against accidental contact with tines of the pinwheel that would otherwise be unnecessarily exposed in an unshrouded pinwheel. Safety is thereby enhanced by limiting the potential for accidental injury or contamination. Also the shroud can be used for the testing of dull nerve sensations while the tines of the pinwheel are used for the testing of sharp nerve sensations.

Another object of the invention is the weighted handle is versatile and can be used with other components. Such components would be designed to be compatible with the coupling mechanism of the handle. An example of such a component would be a disposable skin marking device.

The subject test instrument described herein includes a weighted stainless steel reusable handle with a disposable plastic pinwheel test head releasably attached thereto. The test head includes a first end with coupling arms which are inserted into a receptacle in a first end of the weighted handle. A second end of the test head includes a rotatable pin wheel with a shroud disposed around an upper portion of the pin wheel. The weighted handle includes a hollow elliptical tube with a spring biased ejector bar received inside the tube. One end of the ejector bar, which is used as an ejector button, extends outwardly from a second end of the tube. Upon the completion of a clinical test, the ejector button is pushed and the ejector bar urges the test head outwardly from the first end of the handle.

These and other objects of the present invention will become apparent to those familiar with nerve sensation test instruments from the following detailed description, showing novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a front view of the two piece neurodiagnostic test instrument being held by a tester's right hand and using the thumb and middle finger. In this drawing the weighted handle is gripped and balanced at it's center of gravity.

FIG. 2 is a sectional view of the weighted handle illustrating a spring biased ejector bar received inside an elliptical tube. The ejector bar having one end acting as an ejector button used for ejecting the disposable pinwheel test head.

FIG. 3 is a front view of the two piece neurodiagnostic test instrument being held by the tester's right hand using the thumb and middle finger and gripping the handle to the right of the center of gravity allowing the weight of the handle to fall on the tines of the pinwheel test head.

DESCRIPTION OF THE PREFERRED EMBODIMENTS

Figure 4:
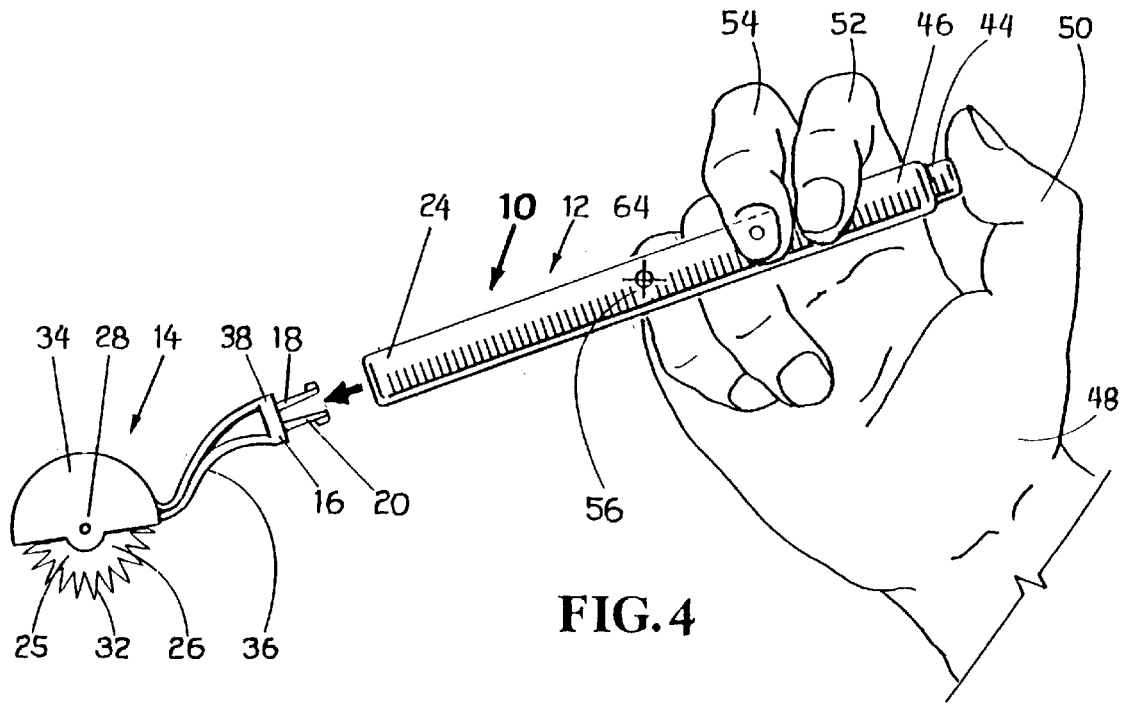
FIG. 4 is a front view of the test instrument with the thumb of the right hand pushing the ejector button for releasing the disposable test head from the weighted handle.

In FIG. 1, a front view of the subject two piece neurodiagnostic test instrument is shown and having general reference numeral 10. The test instrument broadly includes a weighted stainless steel reusable handle and disposable plastic pinwheel test head. The handle and test head are shown having general reference numerals 12 and 14. While a stainless steel handle 12 is mentioned, it can be appreciated that various types of heavy metals and alloys can be used equally well. Likewise, the test head 14 can be made of different types of lightweight materials and having the strength of plastic.

The test head 14 includes a first end 16 with coupling arms 18 and 20 which are inserted into a receptacle 22 in a first end 24 of the weighted handle 12. The coupling arms 18 and 20 and the receptacle 22 are shown in FIG. 2. Referring back FIG. 1, a second end 25 of the test head 14 includes a rotatable pin wheel 26 mounted on a wheel axle 28. The pin wheel 26 also includes a hub 30 and outwardly extending tines 32. A shroud 34 is disposed around an upper portion of the pin wheel 26 and connected to the axle 28. The shroud 34 provides added protection against accidental contact with the tines 32. The shroud 34 is connected to a neck portion 36 which in turn is connected to a stop 38. The stop 38 is connected to one end of the coupling arms 18 and 20. The test head 14 is made of light weight plastic or like materials and typically will have a weight in a range of 1 to 10 grams.

The weighted handle 12 includes a hollow elliptical tube 40 with a spring biased ejector bar 42 received inside the tube 40. One end 44 of the ejector bar 42, which is used as an ejector button, extends outwardly from a second end 46 of the handle 12.

In this drawing, a portion of the physician's right hand 48 is shown with a thumb 50, index finger 52 and middle finger 54. The thumb 50 and middle finger 54 are shown gripping the center of gravity, indicated by a dot 56, along the center of the length of the weighted handle 12. Obviously, if the physician is left handed, the left hand would be used in holding the test instrument 10. In this view, the test instrument is balanced as indicated by arrows 58. As mentioned above, the subject test instrument 10 possesses an optimum weight for consistent pressure during the test procedure. This weight is incorporated into the overall weight of the handle 12 and has been found to be in a range of 50 to 100 grams and more specifically in a range of 65 to 75 grams.

In FIG. 2, a cross section of the handle 12 and a portion of the test head 14 is shown. In this view, the hollow tube 40 has been cut away to expose the ejector bar 42. The bar 42 has a notch 60 therein for receiving a coil spring 62 compressed inside the notch 60 with one end of the spring 62 engaging a dowel pin 64. The dowel pin 64 is inserted through the sides of the hollow tube 40 and one end of the notch 60 for retaining the spring 62 and ejector bar 42 inside the hollow tube 40.

Also shown in this drawing are the two coupling arms 18 and 20 which are spring-like and are biased outwardly. When the arms 18 and 20 are received inside the receptacle 22, they are compressed into a snap fit inside the hollow tube 40. In this manner, the test head 12 is releasably held in the first end 24 of the weighted handle 12. The stop 38 of the test head 14 is used for engagement against the first end 24 of the tube 40.

In FIG. 3, the test instrument is shown being held by the thumb 50 and middle finger 54 of the right hand 48. Also the right hand 48 of the physician has moved along the length of the handle 12 and to the right of the center of gravity 56. When this occurs, the weight of the handle 12 shifts downwardly, as indicated by large arrow 66, onto the weight of the test head 14 for applying a constant pressure on the tines 32 of the pin wheel 26 when engaging a portion of the patient's skin 68 for the testing of sharp nerve sensations. When the testing of sharp nerve sensations is completed, the handle 12 and test head 14 can be turned over and the shroud 34 used for the testing of dull nerve sensations by engaging the patient's skin 68.

In FIG. 4, when the clinical test has been completed, the ejector button 44 is pushed using the thumb 50 of the right hand 48. At this time, the ejector bar 42 is moved inwardly from right to left with a test head engaging end 72 of the bar 42 contacting the two coupling arms 18 and 20 as shown in FIG. 2. At this time the coil spring 62 is compressed inside the notch 60. The coupling arms 18 and 20 are moved outwardly from the receptacle 22 by the test head engaging end 72 thereby releasing the disposable test head 14 and allowing it to drop downwardly and inside a waste receptacle. The waste receptacle is not shown in the drawings. This important feature of the subject invention allows the physician to use the test instrument 10 without contacting the test head 14 after it's use. Also, the risk of exposure to the used test head 14 is reduced since the weighted handle 12 is gripped near the second end 46 of the handle 12 and is at a distance, measured by the length of the handle 12, from the opposite first end 24 of the handle 12 which holds the test head 14. When the ejector button 44 is released by the thumb 50, the compressed spring 62 returns the ejector button 44 outwardly into its relaxed position as shown in FIGS. 1–3.

Figure 5:
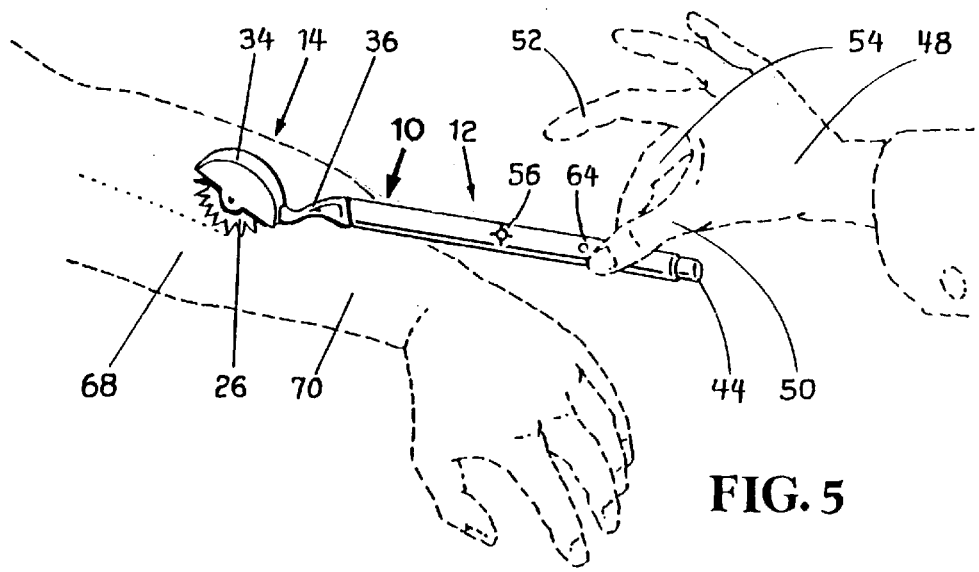
FIG. 5 is a perspective view of the test instrument used by the physician for testing nerve sensation on a patient's left arm.

In FIG. 5, a perspective view of the test instrument 10 is shown and used by the physician for testing nerve sensation on a patient's left arm 70. In the operation of the test instrument 10, the testing physician first removes the disposable plastic test head 14 from it's packaging. The test head 14 is then inserted into the receptacle 22 of the weighted reusable handle 12 as shown in FIG. 2. The instrument 10 is now ready for use.

To test for sharp sensitivity, the physician grasps the handle 12 between his thumb 50 and middle finger 54 and to the right of the center of gravity 56 as shown in FIG. 3. The tines 32 of the test head 14 are now placed on the portion of the skin 68 to be tested. The pin wheel 26 is now stroked along an appropriate area and a subjective response from the patient is recorded. To test for dull sensitivity, the instrument 10 is rotated 180 degrees and the shroud 34 is placed on the portion of the skin 68 being tested. Again, the physician grasps the handle 12 between his thumb 50 and middle finger 54 and strokes the patient's skin 68 along the area being tested. The patients subjective response is recorded. As mentioned above, it is important to the accuracy and the consistency of the test results that only the weight of the instrument 10 be allowed to provide the pressure or force on the skin 68. This is why the instrument 10 is held between the thumb 50 and the middle finger 54. The thumb 50 and middle finger 54 serve as pivot points for the instrument 10 as the pin wheel 26 is stroked along the contours of the patient's skin. Thereby, consistent pressure provided only by the weight of the instrument 10 is applied throughout the test. When used properly as mentioned above, the test instrument 10 provides reliable data to assess nerve function for both sharp and dull sensations.

After the test is completed the test head 14 is considered contaminated. At this point, the test head 14 is automatically ejected and disposed of as described under FIG. 4. The physician tester never needs to come into contact with the contaminated test head 14.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed, except as precluded by the prior art.

The embodiments of the invention for which an exclusive privilege and property right is claimed are defined as follows:

1. A neurodiagnostic test instrument that alone and without additional force applied by a physician provides a necessary weight to achieve accuracy and consistency during an examination procedure, the instrument comprising:

a weighted reusable elongated handle having a first end and a second end, said weighted reusable handle having a weight in a range of 50 to 100 grams;

a disposable pinwheel test head having a first end releasably attached to the first end of said handle; and test head release means disposed in the second end said handle for engaging and releasing said test head without the physician having to touch said test head.

2. The instrument as described in claim 1 wherein a second end of said test head includes a rotatable pin wheel with a plurality of tines therearound, said test head further including a shroud disposed around an upper portion of said pin wheel.

3. The instrument as described in claim 1 wherein said test head release means includes a spring biased ejector bar received inside a hollow tube, said ejector bar and said hollow tube making up said handle, said ejector bar used for engaging and releasing said test head from said handle.

4. The instrument as described in claim 1 wherein said disposable pinwheel test head has a weight in a range of 1 to 10 grams.

5. A neurodiagnostic test instrument that alone and without additional force applied by a physician provides a necessary weight to achieve accuracy and consistency during an examination procedure, the instrument comprising:

a weighted reusable elongated handle having a first end and a second end;

a disposable pinwheel test head having a first end releasably attached to the first end of said handle, said test head having a second end with rotatable pin wheel and a plurality of tines therearound, said test head having a shroud disposed around an upper portion of said pin wheel, said tines used for testing of sharp nerve sensations, said shroud used for testing of dull nerve sensations and providing additional protection from said tines; and test head release means disposed in said handle for engaging and releasing said test head without the physician having to touch said test head, said test head release means including a spring biased ejector bar received inside a hollow tube, said ejector bar and said hollow tube making up said handle, one end of said ejector bar used as an ejector button, said ejector button extending outwardly from a second end of said tube, an opposite end of said ejector bar engaging the first end of said test head.

6. The instrument as described in claim 1 wherein the first end of said test head is one end of an outwardly extend neck portion, said neck portion connected to said shroud, said pin wheel rotatably mounted on said shroud.

7. A neurodiagnostic test instrument that alone and without additional force applied by a physician provides a necessary weight to achieve accuracy and consistency during an examination procedure, the instrument comprising:

a weighted reusable elongated handle having a first end and a second end, said handle having a hollow tube with a spring biased ejector bar slidably received inside said hollow tube, one end of said ejector bar extending outwardly from the second end of said handle and used as an ejector button;

a disposable pinwheel test head having a first end releasably attached to the first end of said handle, said test head having a second end with rotatable pin wheel and a plurality of tines therearound, said test head having a shroud disposed around an upper portion of said pin wheel, said pin wheel rotatably mounted on said shroud, said tines used for testing of sharp nerve sensations, said shroud used for testing of dull nerve sensations;

said ejector bar having an opposite end for engaging and releasing said test head from the first end of said handle; and said test head includes the first end with coupling arms which are inserted into a receptacle in the first end of said weighted handle, said coupling arms in contact with the opposite end of said ejector bar, the first end of said test head connected to a neck portion, said neck portion connected to said shroud.

8. The instrument as described in claim 7 wherein said weighted reusable handle has a weight in a range of 65 to 80 grams.

9. The instrument as described in claim 7 wherein said disposable pinwheel test head has a weight in a range of 1 to 10 grams.

10. The instrument as described in claim 7 wherein said handle includes a notch in said ejector bar for receiving a coil spring compressed therein, said coil spring and said ejector bar held inside said hollow tube by a dowel pin extending through sides of said hollow tube and through a portion of said notch.

* * * * *